United States Patent
Frayling et al.

(10) Patent No.: US 9,771,615 B2
(45) Date of Patent: Sep. 26, 2017

(54) SEQUENCING METHOD

(71) Applicant: BASE4 INNOVATION LTD, Cambridge, Cambridgeshire (GB)

(72) Inventors: Cameron Alexander Frayling, Cambridge (GB); Barnaby Balmforth, Cambridge (GB); Bruno Flavio Nogueira de Sousa Soares, Cambridge (GB); Thomas Henry Isaac, Cambridge (GB); Boris Breiner, Cambridge (GB); Alessandra Natale, Cambridge (GB); Michele Amasio, Cambridge (GB)

(73) Assignee: BASE4 INNOVATION LTD, Cambridge (GB)

( * ) Notice: Subject to any disclaimer, the term of this patent is extended or adjusted under 35 U.S.C. 154(b) by 229 days.

(21) Appl. No.: 14/433,409

(22) PCT Filed: Oct. 4, 2013

(86) PCT No.: PCT/GB2013/052595
§ 371 (c)(1),
(2) Date: Apr. 3, 2015

(87) PCT Pub. No.: WO2014/053854
PCT Pub. Date: Apr. 10, 2014

(65) Prior Publication Data
US 2015/0247192 A1    Sep. 3, 2015

(30) Foreign Application Priority Data
Oct. 4, 2012   (GB) .................................. 1217772.1

(51) Int. Cl.
*C12Q 1/68*      (2006.01)

(52) U.S. Cl.
CPC ......... *C12Q 1/6874* (2013.01); *C12Q 1/6869* (2013.01)

(58) Field of Classification Search
None
See application file for complete search history.

(56) References Cited

U.S. PATENT DOCUMENTS

| 5,528,046 | A | 6/1996 | Ishikawa |
| 5,674,743 | A | 10/1997 | Ulmer |
| 6,316,229 | B1 | 11/2001 | Lizardi et al. |
| 2003/0138831 | A1 | 7/2003 | Kwagh et al. |
| 2010/0184020 | A1 | 7/2010 | Beer |
| 2012/0164633 | A1 | 6/2012 | Laffler |
| 2015/0174576 | A1 | 6/2015 | Van Vilet et al. |

FOREIGN PATENT DOCUMENTS

| JP | 06-148076 | 5/1994 |
| WO | 89/03432 | 4/1989 |
| WO | 2007/120240 | 10/2007 |
| WO | 2009/120372 | 10/2009 |

OTHER PUBLICATIONS

C. Alexander Valencia et al., "Assessment of Target Enrichment Platforms Using Massively Parallel Sequencing for the Mutation Detection for Congenial Muscular Dystrophy", The Journal of Molecular Diagnostics, 2012, vol. 14, No. 3, pp. 233-246.
Deborah J. Boles et al., "Droplet-Based Pyrosequencing Using Digital Microfluidics", Journal of Analytical Chemistry, 2011, vol. 83, pp. 8439-8447.
James Clarke et al., "Continuous base identification for single-molecule nanopore DNA sequencing", Nature Nanotechnology, 2009, vol. 4, pp. 265-270.
Razvan Nutiu et al., "Structure-Switching Signaling Aptamers: Transducing Molecular Recognition into Fluorescence Signaling", Chemistry—A European Journal, 2004, vol. 10, No. 8, pp. 1868-1876.
Yolanda Schaerli et al., "The potential of microfluidic water-in-oil droplets in experimental biology", Molecular Biosystems, Royal Society of Chemistry, 2009, vol. 5, No. 12, pp. 1392-1404.
International Search Report issued Nov. 7, 2013, in International Application No. PCT/GB2013/052595.
Written Opinion of the International Searching Authority issued Nov. 7, 2013, in International Application No. PCT/GB2013/052595.
United Kingdom Search Report issued Feb. 1, 2013, in United Kingdom Patent Application No. 1217772.1.

*Primary Examiner* — David Thomas
(74) *Attorney, Agent, or Firm* — Wenderoth, Lind & Ponack, L.L.P.

(57) ABSTRACT

Disclosed is a method for sequencing a polynucleotide analyte comprising: •a. generating a stream of droplets containing a single nucleotide wherein the order of single nucleotides in the droplet stream corresponds to the sequence of nucleotides in the analyte; •b. introducing into each droplet a plurality of biological probe types each type comprising a different label in an undetectable state and being adapted to capture a different single nucleotide; •c. causing the single nucleotide contained in the droplet to bind to its complementary probe and •d. causing the label to be released from the probe that has bound the nucleotide in a detectable state. The probe is a dumbbell shaped probe comprising fluorescent donor and quencher labels and a single nucleotide gap. After gap repair by a polymerase and a ligase, a restriction enzyme recognition site is cleaved by a restriction enzyme, followed by exonuclease digestion to release the labels.

19 Claims, 1 Drawing Sheet

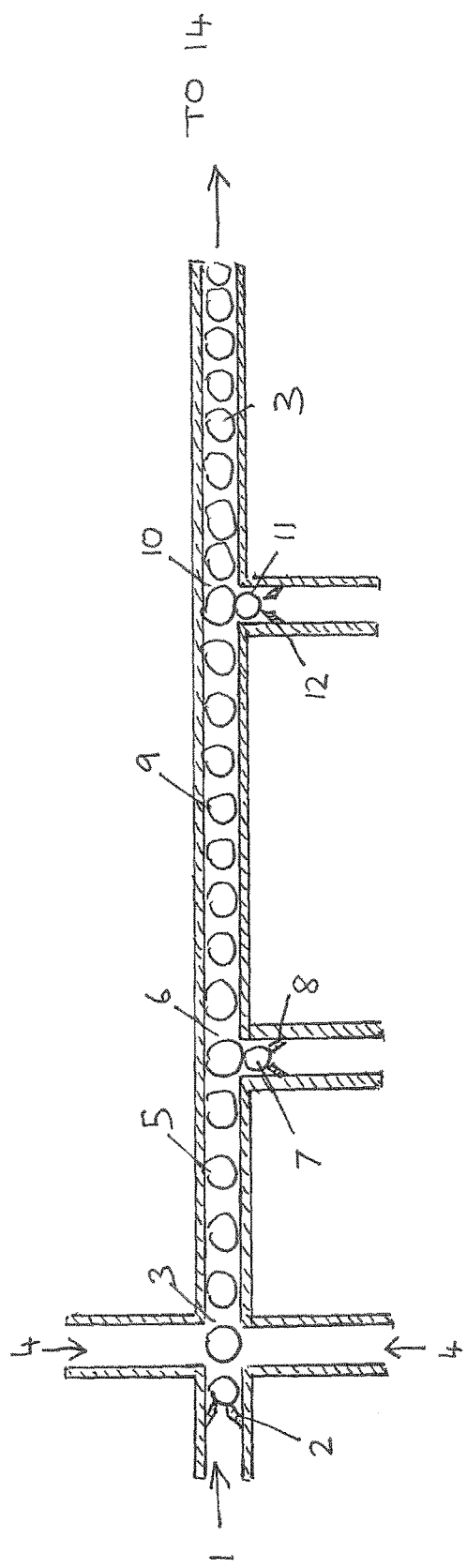

SEQUENCING METHOD

The present invention relates to a method for determining the sequence of nucleotide bases in polynucleotides derived, for example, from naturally occurring DNA or RNA.

Next generation sequencing of genetic material is already making a significant impact on the biological sciences in general and medicine in particular as the unit cost of sequencing falls in line with the coming to market of faster and faster sequencing machines. For example, our co-pending application WO 2009/030953 discloses a new fast sequencer in which inter alia the sequence of nucleotide bases or base pairs in a single or double stranded polynucleotide sample (e.g. naturally occurring RNA or DNA) is read by translocating the same through a nano-perforated substrate provided with plasmonic nanostructures juxtaposed within or adjacent the outlet of the nanopores. In this device, the plasmonic nanostructures define detection windows (essentially an electromagnetic field) within which each nucleotide base (optionally labelled) is in turn induced to fluoresce or Raman scatter photons in a characteristic way by interaction with incident light. The photons so generated are then detected remotely, multiplexed and converted into a data stream whose information content is characteristic of the nucleotide base sequence associated with the polynucleotide. This sequence can then be recovered from the data stream using computational algorithms embodied in corresponding software programmed into a microprocessor integral therewith or in an ancillary computing device attached thereto.

Another apparatus for fast sequencing polynucleotides is described for example in U.S. Pat. No. 6,627,067, U.S. Pat. No. 6,267,872 and U.S. Pat. No. 6,746,594. In its simplest form, this device employs electrodes, instead of plasmonic nanostructures, to define the detection window across the substrate or in or around the outlet of the nanopore. A potential difference is then applied across the electrodes and changes in an electrical property of the ionic medium flowing therebetween, as a consequence of the electrophoretic translocation of the polynucleotide and associated electrolyte through the nanopore, is measured as a function of time. In this device, as the various individual nucleotide bases pass through the detection window they continuously block and unblock it causing 'blocking events' which give rise to characteristic fluctuations in current flow or resistivity. These fluctuations are then used to generate a suitable data stream for analysis as described above.

The generation of stable droplet streams, especially microdroplet streams, is another developing area of technology that already has applications in molecular biology. For example, U.S. Pat. No. 7,708,949 discloses a novel microfluidic method for generating stable water droplets in oil whilst for example US2011/0250597 describes utilisation of this technology to generate microdroplets containing a nucleic acid template (typically a polynucleotide DNA or RNA fragment) and a plurality of primer pairs that enable the template to be amplified using the polymerase chain reaction. Other patent applications relating to this approach and to the field generally include US 2010/184020, US2012/0164633, US2012/0122714, US2011/0000560, US2010/01376163, US2010/0022414 and US2008/0003142. J. Molecular Diagnostics 14(3) 233-246 (2012) describes the use of this microdroplet PCR method in identifying the genetic mutations associated with congenital muscular dystrophy.

WO2007/120240 and J. Anal. Chem. 83 8439-8447 (2011) each describe a droplet-based approach to characterising nucleic acids involving pyrosequencing.

Likewise, biological probes, which typically comprise single-stranded oligonucleotides of known sequence order less than 1000 nucleotides long, are widely used in analytical molecular biology. Such probes typically work by attaching themselves to the target (for example one derived from the DNA of a naturally-occurring pathogen) when sufficient sequence complimentarity exists between the nucleotide bases of the probe and the target. Typically the nucleotides of such probes are labelled with detectable elements such as radioactive or fluorescent markers so that when the probe is used to treat an analyte solution or substrate in or on which the target is thought to have been captured, the presence or absence of the target is revealed by searching for and detecting the detection element's characteristic detection property.

One class of such probes is represented by materials known in the art as 'molecular beacons' as for example described in in WO02/06531 or U.S. Pat. No. 8,211,644. These probes are comprised of single-stranded oligonucleotides which have been in effect folded back onto themselves to create a residual single-stranded loop which acts as the probe's sensor and a short stem where the nucleotides adjacent the two ends are bound to each other through complimentary nucleotide base pairing; thereby creating a double-stranded region. This arrangement, which can be likened to a hairpin in which the single-stranded loop is attached to complimentary strands of the same end of a notional double-stranded oligonucleotide, is highly strained. To the free 3' and 5' ends of the oligonucleotide (now adjacent to one another and at the remote end of the stem) are respectively attached a fluorophore and a quencher. Their geometric proximity to each other then ensures that no significant fluorescence occurs. In use, the target binds to the single-stranded loop causing additional strain so that when the probe is heated the stem unzips causing distancing of the fluorophore and quencher and allowing the former to fluoresce.

We have now developed a new method of determining the sequence of nucleotide bases in a polynucleotide sample which is different from those described above and in which individual, single nucleotide-containing droplets in a stream derived from, and whose ordering corresponds to, the nucleotide base pair sequence of, the sample are interrogated after having been treated with certain labelled biological probes. Typically the result of this treatment is to generate in each droplet one or more detectable elements characteristic of the particular nucleotide base associated with the nucleotide therein. A feature of this method is the use of new biological probes in which the detectable elements are essentially undetectable unless specifically activated by a sequence of biochemical/enzymatic reactions which liberate one or a cascade of the detectable elements from the probe in a detectable state.

According to the present invention, there is therefore provided a method for determining the sequence of nucleotide bases in a polynucleotide analyte characterised by the steps of:
  a. generating a stream of droplets at least some of which contain a single nucleotide and wherein the order of single nucleotides in the droplet stream corresponds to the sequence of nucleotides in the analyte;
  b. introducing into each droplet a plurality of biological probe types each type (i) comprising a different detectable element in an undetectable state and (ii) being adapted to capture a different complimentary single nucleotide from which the analyte is constituted;

c. causing the single nucleotide contained in the droplet to bind to its complimentary probe to create a used probe and d. causing the detectable element to be released from the used probe in a detectable state.

In a preferred embodiment of the invention each biological probe comprises a single-stranded nucleotide region the ends of which are attached to two different double-stranded oligonucleotide regions wherein at least one of the oligonucleotide regions comprises detectable elements having a characteristic detection property and wherein the detectable elements are so arranged on the oligonucleotide region that the detectable property is less detectable than when the same number of detectable elements are bound to a corresponding number of single nucleotides.

In one preferred embodiment, the detectable elements comprise fluorophores and the probe itself is essentially non-fluorescing at those wavelengths where the fluorophores are designed to be detected. Thus, although a fluorophore may exhibit general, low-level background fluorescence across a wide part of the electromagnetic spectrum there will typically be one or a small number of specific wavelengths or wavelength envelopes where the intensity of the fluorescence is at a maximum. It is at one or more of these maxima where the fluorophore is characteristically detected that essentially no fluorescence should occur. In the context of the present invention by the term 'essentially non-fluorescing' or equivalent wording is meant that the intensity of fluorescence of the total number of fluorophores attached to the probe at the relevant characteristic wavelength or wavelength envelope is less than 25%; preferably less than 10%; more preferably less than 1% and most preferably less than 0.1% of the corresponding intensity of fluorescence of an equivalent number of free fluorophores.

In principle, any method can be used to ensure that in the probe's unused state the fluorophores are essentially non-fluorescing. One approach is to additionally attach quenchers in close proximity thereto. Another is based on the observation that when multiple fluorophores are attached to the probe in close proximity to each other they tend to quench each other sufficiently well that the criterion described in the previous paragraph can be achieved without the need for quenchers. In this context of this patent, what constitutes 'close proximity' between fluorophores or between fluorophores and quenchers will depend on the particular fluorophores and quenchers used and possibly the structural characteristics of the oligonucleotide region(s). Consequently, it is intended that this term be construed with reference to the required outcome rather than any particular structural arrangement on the probe. However, and for the purposes of providing exemplification only, it is pointed out that when adjacent fluorophores or adjacent fluorophores and quenchers are separated by a distance corresponding to the characteristic Förster distance (typically less than 5 nm) sufficient quenching will be achieved Preferably, at least one of the oligonucleotides which comprise the probe is labelled with up to 20, preferably up to 10 and most preferably up to 5 fluorophores. To obtain maximum advantage, it is preferred that at least one of the oligonucleotide regions is labelled with at least 2 preferably at least 3 fluorophores. Consequently, ranges constructed from any permutation of these maxima and minima are specifically envisaged herein. If quenchers are employed, it is likewise preferred that the probe is labelled with up to 20, preferably up to 10 and most preferably up to 5 of the same.

Whilst it is envisaged that more than one type of fluorophore can be attached to the probe, for example to give it a characteristic fingerprint, it is preferred that all the fluorophores attached to a given probe are of the same type. In one embodiment, the fluorophores and quenchers are on different strands of the oligonucleotide region or opposite each other where they are created by folding a single-stranded oligonucleotide precursor.

As regards the fluorophores themselves, they can in principle be chosen from any of those conventionally used in the art including but not limited to xanthene moieties e.g. fluorescein, rhodamine and their derivatives such as fluorescein isothiocyanate, rhodamine B and the like; coumarin moieties (e.g. hydroxy-, methyl- and aminocoumarin) and cyanine moieties such as Cyt, Cy3, Cy5 and Cy7. Specific examples include fluorophores derived from the following commonly used dyes: Alexa dyes, cyanine dyes, Atto Tec dyes, and rhodamine dyes. Examples also include: Atto 633 (ATTO-TEC GmbH), Texas Red, Atto 740 (ATTO-TEC GmbH), Rose Bengal, Alexa Fluor™ 750 $C_5$-maleimide (Invitrogen), Alexa Fluor™ 532 $C_2$-maleimide (Invitrogen) and Rhodamine Red $C_2$-maleimide and Rhodamine Green as well as phosphoramadite dyes such as Quasar 570. Alternatively, a quantum dot or a near infra-red dye such as those supplied by LI-COR Biosciences can be employed. The fluorophore is typically attached to the oligonucleotide via a nucleotide base using chemical methods known in the art.

Suitable quenchers include those which work by a Förster resonance energy transfer (FRET) mechanism. Examples of commercially available quenchers which can be used in association with the above mentioned-fluorophores include but are not limited to DDQ-1, Dabcyl, Eclipse, Iowa Black FQ and RQ, IR Dye-QC1, BHQ-1, -2 and -3 and QSY-7 and -21.

The single-stranded nucleotide region is comprised of one nucleotide only making the probe extremely selective for the detection of the free nucleotide having a complimentary nucleotide base. In practice, for DNA this means that the nucleotide region will be adapted to bind to nucleotides whose characteristic nucleotide base is selected from guanine, cytosine, adenine and thymine or in the case of RNA from guanine, cytosine, adenine and uracil. However other nucleotides corresponding to other nucleotide bases (e.g. those constitutive of other synthetic polynucleotides) can be employed if so desired. When sequencing DNA or RNA therefore a mixture of four different probes each selective for a different complimentary nucleotide base and each employing a different detectable element will typically be used. In a preferred embodiment, each probe will have different detectable elements e.g. labelled with different fluorophores fluorescing at different characteristic wavelengths or wavelength envelopes. Thus, when the characteristic fluorescence is detected the nucleotide can be uniquely identified.

Turning to the double-stranded oligonucleotide region(s), it is preferred that they are derived or derivable from two oligonucleotide precursors, each preferably closed looped, or from a common single-stranded oligonucleotide precursor by folding the latter's two ends back on themselves to create two closed loop oligonucleotide regions with an intermediate gap constituting the single-stranded nucleotide region. In all cases, the effect is the same; adjacent to the ends of the single-stranded nucleotide region will be 3' and 5' free ends on the other strand of the double-stranded oligonucleotide region(s) to which the corresponding 5' and 3' ends of the target can be attached. Thus use of the probe thus involves a process of attaching the single-stranded nucleotide region to the target single nucleotide by joining up to said 3' and 5' ends to generate a used probe which is double-stranded along it whole length.

Suitably, the double-stranded oligonucleotide region(s) are up to 50 nucleotide pairs long, preferably up to 45 nucleotide pairs, more preferably in the range 5 to 40 nucleotide pairs and most preferably in the range 10 to 30 nucleotides. Longer oligonucleotide regions may be used but the potential risk that access to the nucleotide region by the single nucleotide target may become restricted through entanglement makes this embodiment potentially less attractive.

It is preferred that the detectable elements bound to the oligonucleotides are located remote from the single-stranded nucleotide region. Where two discrete oligonucleotides are employed it is preferred that the detectable elements are located or clustered at or towards one or both of the ends thereof which are remote from the nucleotide region. Finally, it is preferred that at least one of the oligonucleotides comprises at least one restriction enzyme recognition site preferably adjacent the region where the detectable elements are located or clustered. Such a restriction enzyme recognition site will typically comprise a specific sequence of from 2 to 8 nucleotide pairs. In an embodiment of the invention the restriction enzyme recognition site is created by binding of the single nucleotide to the nucleotide region.

The biological probes preferably used in the method of the present invention can in principle be manufactured by any of the nucleotide assembly methodologies known in the art including the H-phosphonate method, the phosophodiester synthesis, the phosphotriester synthesis and the phosphite triester synthesis. Preferred are methods employing nucleotide phosphoramadite building blocks on account of their reactivity. In these methods, synthesis occurs by sequential addition of the chosen nucleotide phosphoramadite to the growing nucleotide chain at the 5' position in a cyclic four-step process involving de-blocking, coupling, capping and oxidation. The cyclic nature of this process makes it especially amenable to automation and machines to do this are readily available on the market. Where quenchers and/or fluorophores are to be introduced the appropriately labelled nucleotide phosphoramadite is employed at the required point. In a most preferred embodiment the phosphoramadite method is used to make a single-stranded oligonucleotide precursor which is folded by a cycle of rapid heating and slow cooling into a probe having the desired characteristics.

In step (a) of the method of the present invention a stream of droplets at least some of which contain a single nucleotide is generated. For sequencing purposes, it is important the order of the single nucleotides in the droplet stream correspond to the sequence of nucleotides in the analyte. Suitably such an ordered droplet stream is created by introducing the single nucleotides strictly in turn into a corresponding stream of empty droplets. This can be achieved for example by passing an aqueous stream through a regime where single nucleotides are being liberated from the analyte and then passing the stream through an orifice from which it exits into a stream of immiscible carrier liquid. To avoid the risk that a given droplet contains more than one single nucleotide it is preferred to release the single nucleotides into the aqueous stream at a rate such that each filled droplet is separated by between 1 and 20 (preferably 2 and 10) empty ones. Thereafter the stream of filled droplets in the carrier is caused to flow along a flow path, suitably a microfluidic flow path at a rate and in a manner such that the droplets are maintained in a discrete state and do not have the opportunity to coalesce with each other. In an example of one particularly suitable embodiment the carrier comprises a mixture of fluorocarbon oil (such as 3M Fluorinert FC40) and a fluorophilic surfactant (such as Sphere Fluidics Picosurf 1), and the aqueous droplets contain a mixture of water, glycerol, ionic salts and other additives necessary for the probe reaction. Preferably the microfluidic flow path is treated with a coating or surface modification which causes it to have hydrophobic properties, thereby preventing the microdroplets interacting with or adhering to it. More preferably this surface modification is also oleophilic and causes the formation of a coating layer of the carrier on the flow path and further isolating the aqueous droplets from the channel walls. Suitably the droplets employed have a diameter less than 100 microns, preferably less than 50 microns (e.g. less than 20 microns) more preferably less than 10 microns and even more preferably less than 5 microns. Most preferably of all their diameters are in the range 2 to 20 microns. Typically the single nucleotides are those derived from a naturally occurring polynucleotide analyte preferably naturally occurring DNA or RNA.

In step (b) of the method a plurality of biological probes preferably a plurality of those described above are introduced into each droplet. Preferably a mixture of all the probes required to detect all the analytes various nucleotides will be introduced into each droplet. Most preferably of all, these probes will each have multiple detectable elements in an undetectable state attached thereto and at least one restriction enzyme recognition site or the precursor thereof. Introduction of the probe into the droplet can be done by mixing of two streams prior to droplet generation but after nucleotide release, by injection into the droplets, or by preferably bringing together the droplet stream with a second droplet stream (each droplet of which contains the probe mixture) under conditions where droplets from the two streams coalesce with one another in a sequential way to create a third stream of larger droplets containing both the single nucleotide and the probe(s). At the same time, it is preferred to introduce into each droplet a polymerase and/or a ligase; although these items can be introduced separately if so desired. Once this introduction has occurred, in step (3) the single nucleotide in the droplet is caused to bind to its complimentary probe in the probe mixture at the expense of the others. In a preferred embodiment this binding is caused to take place sequentially through first the use of the polymerase to bind the 5' end of the single nucleotide to a 3' end of the oligonucleotide and then a ligase to join the remaining free ends of the single nucleotide and the oligonucleotide or other oligonucleotide together. A wide range of polymerases and ligases can be used including but are not limited to those derived from readily available bacterial sources such as bacteriophage T4, *Escherichia Coli* and *Thermus Aquaticus* (Taq). Preferably this step is carried out in an aqueous medium in the presence of excess probe with suitably the molar ratio of target to probe being in the range 1:1 to 1:2000, preferably 1:1 to 1:200, more preferably 1:2 to 1:50 with 1:20 to 1:50 being most preferred. Alternatively, a ratio in the range 1:5 to 1:20 can be employed.

The product of step (c), i.e. a droplet now containing the single nucleotide bound to its complimentary probe (hereinafter called the used probe) and the other unreacted probes is next treated in step (d) so that the detectable elements on the used probe are released into the droplet medium in a detectable state. This enables them to be then detected using conventional techniques. For example, when the detectable elements in the probe and the used probe are non-fluorescing fluorophores, step (d) causes them to be liberated from the latter (but not the former or the other probe types in the droplet) in a form which enables them to begin fluorescing fully. The fluorescence so generated can then be detected and measured in each droplet using conventional optical or spectroscopic techniques to provide an output data set or data stream characteristic of the original analyte sequence. Suitably, step (d) is caused to occur by introducing into the droplet, e.g. by using the injection or preferably a second coalescence of the type described above, a restriction enzyme (restriction endonuclease) and an exonuclease. In this example, and where the detectable elements are fluorophores, release of the fluorophore comes about by first the restriction enzyme making a double-stranded cut in the used probe at the restriction enzyme recognition site mentioned above. The short fragments so created are then degraded further by the exonuclease into single nucleotides some of which will be labelled with fluorophores. When the probe comprises multiple quenched fluorophores, a preferred embodiment, this leads to a cascade of liberated fluorophores which, by virtue of them now being separated from each other and/or their associated quenchers, are now free to fluoresce in the normal way. Preferably, this fluorescence is detected using a photodetector or an equivalent device tuned to the characteristic fluorescence wavelength or wavelength envelope of the fluorophore. In an example of one embodiment, the photodetector comprises a high-sensitivity sCMOS camera (Zyla 10-tap sCMOS, Andor Technology) upon which an image of the droplets is formed using a combination of an objective lens (UPLSAPO 60×W, Olympus) and a standard achromatic tube lens. Excitation of the fluorescence emission in this embodiment uses a set of lasers which are introduced to the optical path through a dichroic mirror. An external scanning apparatus deflects the laser beams across the droplets. The fluorescence emission resulting from this process causes the photodetector to generate an electrical signal which can be processed and analysed in the normal way. As mentioned above it is preferred to detect the detectable elements by optical or spectroscopic means.

Typically step (d) is also carried out in an aqueous medium and with an excess of enzymes. In order to avoid degrading unused biological probe, it is preferred that the restriction enzyme recognition site is that formed by adding the single nucleotide to the single-stranded nucleotide region or alternatively that the restriction enzyme is chosen so that it will not react with double-stranded oligonucleotides which contain nicks therein. The restriction enzyme will thus be chosen with the characteristics of the restriction enzyme site in mind and will in particular be one which shows high fidelity for the site if the probes are going to perform optimally. Suitable exonucleases include Dnase I (RNase-free), Exonuclease I or III (ex *E. coli*), Exonuclease T, Exonuclease V (RecBCD), Lambda Exonuclease, Micrococcal Nuclease, Mung Bean Nuclease, Nuclease BAL-31, RecJ$_f$, T5 Exonuclease and T7 Exonuclease.

Typically the droplet flow rate through the device is in the range 50 to 3000 droplets per second preferably 100 to 2000.

In an example of one suitable embodiment, a co-flowing aqueous stream containing two sets of reagents is used to generate the droplets. By combining two streams close to the site of droplet generation, constituents of the reaction mixture can be held separately for the longest possible time.

The droplet sequencing method of the present invention is now illustrated with reference to the following device in which:

FIG. 1 schematically illustrates a microfluidics unit in which droplets, each containing a single nucleotide, are made to undergo reaction with the biological probes as described above.

Through a ten micron diameter microfluidic tube flows an aqueous stream 1 containing single nucleotides obtained from a 100 nucleotide base polynucleotide analyte derived from human DNA and Klenow fragment polymerase. The order of nucleotides in the droplet stream corresponds to the sequence of the analyte. The single nucleotide stream may be generated by degradation of a single strand of the analyte which is located on the internal surface of the tube. 1 emerges from a droplet head 2 into a first chamber 3 where it is contacted with one or more streams of light silicone oil 4. The velocities of these streams are chosen to avoid turbulent mixing and to create substantially aqueous spherical droplets 5 suspended in the oil each having a diameter of approximately eight microns. A stream of 5 is then carried forward along a second microfluidic tube of the same diameter at a rate of 1000 droplets per second to a second chamber 6 into which a second stream of five micron aqueous spherical droplets 7 is fed using a second droplet head 8. Droplets 5 and 7 are caused to coalesce in a sequential fashion to form enlarged aqueous droplets 9 approximately nine microns in diameter. Each of 7 contain the probe mixture described below, E. coli DNA ligase and four restriction enzymes each suitable for uniquely cutting a different used probe type at a unique recognition site created by the binding of the relevant single nucleotide. In this example, the restriction enzyme recognition site is four nucleotide bases long. The molar ratio of the single nucleotide to each probe in each of 9 is 1:20.

A stream of 9 is next carried forward at the same rate via microfluidic tubing into a third chamber 10 where it is contacted with a third stream of five micron aqueous spherical droplets 11 also fed thereto through droplet head 12. The time taken for each of 9 to move between the chambers is 30 minutes.

9 and 11 are caused to coalesce in 10 to produce droplets 13 (approximately ten microns in diameter). Each of 11 contains Lambda Exonuclease in a catalytic amount. A stream of droplets 13 is then carried forward into the inlet of detection system. During this time and within the cartridge, the exonuclease then degrades the chopped-off oligonucleotide fragment generated by the restriction enzyme in the process liberating a cascade of single nucleotides with now unquenched fluorophores attached thereto. The contents of the droplets are buffered at a pH in the range 7.9 to 8 at all times.

The detection system (not shown) typically comprises a cartridge consisting of a channel or reservoir in which each of the droplets in 13 is stored under conditions which ensure their integrity. Said cartridge is provided with at least one face made of transparent plastic or like material enabling each droplet so stored to be interrogated with incident light from a microscope/laser/photodetector. This in turn causes the liberated fluorophores in each droplet to fluoresce in a way characteristic of the single nucleotide it originally contained (or not at all if the droplet was originally empty). Thus as the droplets are interrogated in turn the sequence of nucleotide bases in the original polynucleotide can in effect be read off. In use, the cartridge is filled up, sealed and, once the exonuclease has finished releasing the fluorophores (typically within 1 to 2 hours), interrogated. If desired the droplet carrier liquid can be or can contain an organic or inorganic monomer (e.g. an epoxide) polymerisation of which can be initiated by ultra-violet light to create a clear, solid matrix for the droplets enabling the cartridges to be easily stored indefinitely if so required.

The following illustrates how a probe mixture suitable for use in the device described above can be prepared.

A 103 nucleotide single-stranded oligonucleotide precursor (ex. ATDBio) having the nucleotide base sequence:

(5')GGCACGATGGXXAXXGCCCGCACTTCAGCGGGCAAYAACCATCGTG
CCTGCAGGCTCGACCTTTATTCGCGGCACTTCAGCCGCGAATAAAGGTCG
AGCCTGC(3') (SEQ ID NO: 1)

wherein X are T bases labelled with Quasar 570 (fluorophore) and wherein Y are T bases labelled with BHQ-2 quencher, is folded about the 49$^{th}$ nucleotide base by heating an aqueous solution of it to 95° C. and then cooled slowly back to room temperature at a rate of 10 minutes per ° C. At the end of this time, a closed loop probe according to the present invention is formed in which the 49$^{th}$ nucleotide base (here T) comprises the single-stranded nucleotide region and two double-stranded oligonucleotides, respectively 24 and 27 nucleotide base pairs long, flank it.

Next, three other probes suitable for capturing the other three nucleotide bases are prepared by starting from three similar 103 nucleotide base oligonucleotides where the 49$^{th}$ base in the above is A, G or C as the case may be. In these cases the X bases comprise T bases labelled respectively with: Fluorescein (517 nm), Texas Red (612 nm) and cyanine-5 (667 nm). A probe mixture is then prepared by mixing the four probes in equimolar amounts.

The invention claimed is:

1. A method for determining the sequence of nucleotide bases in a polynucleotide analyte, the method comprising steps of:
   a. generating a stream of single nucleotides selected from the group consisting of single nucleoside monophosphates, single nucleoside diphosphates and single nucleotide triphosphates by progressive enzymatic digestion of the analyte and thereafter generating a corresponding stream of droplets at least some of which contain one of the single nucleotides and wherein the order of the single nucleotides in the droplets in the droplet stream corresponds to the sequence of nucleotides in the analyte;
   b. introducing into each droplet a plurality of single nucleotide compatible biological probe types each type (i) comprising a single-stranded nucleotide region the ends of which are attached to two different double-stranded oligonucleotide regions wherein at least one of the oligonucleotide regions comprises detectable elements having a characteristic detection property and wherein the detectable elements are so arranged on the oligonucleotide region that the detectable property is less detectable than when the same number of detectable elements are each bound to separate oligonucleotides and (ii) being adapted to capture a different complimentary single nucleotide from which the analyte is constituted;
   c. using a polymerase and a ligase to cause the single nucleotide contained in the droplet to bind to its complimentary probe to create a used probe; and
   d. causing the detectable element to be released from the used probe in a detectable state.

2. The method as claimed in claim 1, characterised in that the detectable elements comprise fluorophores and the probe is non-fluorescing at one or more wavelengths or wavelength envelopes at which the fluorophores are to be detected.

3. The method as claimed in claim 2, characterised in that the oligonucleotide regions comprise first and second double-stranded oligonucleotides connected together by the single-stranded nucleotide region and wherein at least one of said double-stranded oligonucleotides is labelled with multiple fluorophores in close proximity to each other.

4. The method as claimed in claim 1, characterised in that at least one of the double-stranded oligonucleotides is labelled with quenchers in close proximity to the fluorophores.

5. The method as claimed in claim 1, characterised in that the single nucleotide is comprised of a nucleotide base selected from one of thymine, guanine, cytosine, adenine and uracil.

6. The method as claimed in claim 1, characterised in that each double-stranded oligonucleotide is comprised of from 10 to 30 nucleotide pairs.

7. The method as claimed in claim 1, characterised in that up to 10 nucleotide pairs in a double-stranded oligonucleotide are labelled with a fluorophore.

8. The method as claimed in claim 1, characterised in that up to 10 nucleotide pairs in a double-stranded oligonucleotide are labelled with a quencher.

9. The method as claimed in claim 1, characterised in that the biological probe comprises at least one restriction enzyme recognition site.

10. The method as claimed in claim 9, characterised in that the restriction enzyme recognition site is created by attaching the single nucleotide to the single-stranded nucleotide region of the biological probe.

11. The method as claimed in claim 1, characterised in that one or more of the detectable elements are fluorophores.

12. The method as claimed in claim 1, characterised in that the used probe comprises a restriction enzyme recognition site which has been formed by the attaching of the single nucleotide to the single-stranded nucleotide region.

13. The method as claimed in claim 1, characterised in that each of the biological probes has a different detectable element.

14. The method as claimed in claim 1, characterised in that step c is carried out in the presence of a polymerase and a ligase.

15. The method as claimed in claim 1, characterised in that step d is carried out in the presence of a restriction enzyme and an exonuclease.

16. The method as claimed in claim 1, characterised in that the detectable elements are detected by an optical or spectroscopic means.

17. The method as claimed in claim 1, characterised in that the stream of droplets comprises a stream of aqueous droplets in an oil carrier.

18. The method as claimed in claim 17, characterised in that the droplets are less than 50 microns in diameter.

19. The method as claimed in claim 1, characterised in that the polynucleotide analyte is derived from naturally occurring DNA and RNA.

\* \* \* \* \*

SEQUENCE LISTING

<160> NUMBER OF SEQ ID NOS: 4

<210> SEQ ID NO 1
<211> LENGTH: 103
<212> TYPE: DNA
<213> ORGANISM: Artificial Sequence
<220> FEATURE:
<223> OTHER INFORMATION: Biological probe
<220> FEATURE:
<221> NAME/KEY: modified_base
<222> LOCATION: (11)..(12)
<223> OTHER INFORMATION: Bases are labelled with Quasar 570
      (fluorophore)
<220> FEATURE:
<221> NAME/KEY: modified_base
<222> LOCATION: (14)..(15)
<223> OTHER INFORMATION: Bases are labelled with Quasar 570
      (fluorophore)
<220> FEATURE:
<221> NAME/KEY: modified_base
<222> LOCATION: (36)..(36)
<223> OTHER INFORMATION: Base is labelled with BHQ-2 quencher

<400> SEQUENCE: 1
ggcacgatgg ttattgcccg cacttcagcg ggcaataacc atcgtgcctg caggctcgac      60
ctttattcgc ggcacttcag ccgcgaataa aggtcgagcc tgc                       103

<210> SEQ ID NO 2
<211> LENGTH: 103
<212> TYPE: DNA
<213> ORGANISM: Artificial sequence
<220> FEATURE:
<223> OTHER INFORMATION: Biological probe
<220> FEATURE:
<221> NAME/KEY: modified_base
<222> LOCATION: (11)..(12)
<223> OTHER INFORMATION: Bases are labelled with Fluorescein (517nm)
<220> FEATURE:
<221> NAME/KEY: modified_base
<222> LOCATION: (14)..(15)
<223> OTHER INFORMATION: Bases are labelled with Fluorescein (517nm)
<220> FEATURE:
<221> NAME/KEY: modified_base
<222> LOCATION: (36)..(36)
<223> OTHER INFORMATION: Base is labelled with BHQ-2 quencher

<400> SEQUENCE: 2
ggcacgatgg ttattgcccg cacttcagcg ggcaataacc atcgtgccag caggctcgac      60
ctttattcgc ggcacttcag ccgcgaataa aggtcgagcc tgc                       103

<210> SEQ ID NO 3
<211> LENGTH: 103
<212> TYPE: DNA
<213> ORGANISM: Artificial sequence

```
<220> FEATURE:
<223> OTHER INFORMATION: Biological probe
<220> FEATURE:
<221> NAME/KEY: modified_base
<222> LOCATION: (11)..(12)
<223> OTHER INFORMATION: Bases are labelled with Texas Red (612nm)
<220> FEATURE:
<221> NAME/KEY: modified_base
<222> LOCATION: (14)..(15)
<223> OTHER INFORMATION: Bases are labelled with Texas Red (612nm)
<220> FEATURE:
<221> NAME/KEY: modified_base
<222> LOCATION: (36)..(36)
<223> OTHER INFORMATION: Base is labelled with BHQ-2 quencher

<400> SEQUENCE: 3
ggcacgatgg ttattgcccg cacttcagcg ggcaataacc atcgtgccgg caggctcgac      60
ctttattcgc ggcacttcag ccgcgaataa aggtcgagcc tgc                       103

<210> SEQ ID NO 4
<211> LENGTH: 103
<212> TYPE: DNA
<213> ORGANISM: Artificial sequence
<220> FEATURE:
<223> OTHER INFORMATION: Biological probe
<220> FEATURE:
<221> NAME/KEY: modified_base
<222> LOCATION: (11)..(12)
<223> OTHER INFORMATION: Bases are labelled with cyanine-5 (667nm)
<220> FEATURE:
<221> NAME/KEY: modified_base
<222> LOCATION: (14)..(15)
<223> OTHER INFORMATION: Bases are labelled with cyanine-5 (667nm)
<220> FEATURE:
<221> NAME/KEY: modified_base
<222> LOCATION: (36)..(36)
<223> OTHER INFORMATION: Base is labelled with BHQ-2 quencher

<400> SEQUENCE: 4
ggcacgatgg ttattgcccg cacttcagcg ggcaataacc atcgtgcccg caggctcgac      60
ctttattcgc ggcacttcag ccgcgaataa aggtcgagcc tgc                       103
```